United States Patent
Monchalin et al.

(10) Patent No.: US 8,004,689 B2
(45) Date of Patent: Aug. 23, 2011

(54) METHOD OF ASSESSING BOND INTEGRITY IN BONDED STRUCTURES

(75) Inventors: Jean-Pierre Monchalin, Montreal (CA); Alain Blouin, Montreal (CA); Benjamin Campagne, Marcoussis (FR)

(73) Assignee: National Research Council of Canada, Ottawa, Province of Ontario (CA)

( * ) Notice: Subject to any disclaimer, the term of this patent is extended or adjusted under 35 U.S.C. 154(b) by 406 days.

(21) Appl. No.: 12/227,115

(22) PCT Filed: May 9, 2007

(86) PCT No.: PCT/CA2007/000851
§ 371 (c)(1),
(2), (4) Date: Nov. 7, 2008

(87) PCT Pub. No.: WO2007/128138
PCT Pub. Date: Nov. 15, 2007

(65) Prior Publication Data
US 2009/0168074 A1 Jul. 2, 2009

Related U.S. Application Data

(60) Provisional application No. 60/799,004, filed on May 10, 2006, provisional application No. 60/837,613, filed on Aug. 15, 2006.

(51) Int. Cl.
*G01B 11/02* (2006.01)
*G01B 9/02* (2006.01)
*G01N 21/41* (2006.01)
*G01N 29/04* (2006.01)

(52) U.S. Cl. .......................................... 356/502; 73/657
(58) Field of Classification Search .................. 356/502; 73/655, 657
See application file for complete search history.

(56) References Cited

U.S. PATENT DOCUMENTS 6,181,431 B1 * 1/2001 Siu ................................ 356/502
6,490,047 B2 * 12/2002 Siu ................................ 356/502

* cited by examiner

*Primary Examiner* — Patrick J Connolly
(74) *Attorney, Agent, or Firm* — Ira S. Dorman

(57) ABSTRACT

A technique for acoustic detection of a disbond within a bonded structure involves thermal excitation of the surface of the bonded structure to induce a lifting and membrane vibration and is applicable to laminates and coated structures, as well as foam core structures or a honeycomb structures. The technique does not require access to both sides of the bonded structure. A large etendue interferometer is used to provide surface displacement measurement. The surface displacement measurement can be analyzed both by frequency or amplitude to determine existence of a disbond by membrane vibration, and further a thickness of the disbond can be determined using traditional pulse-echo time analysis. The technique may allow detection of stick bonds.

29 Claims, 16 Drawing Sheets

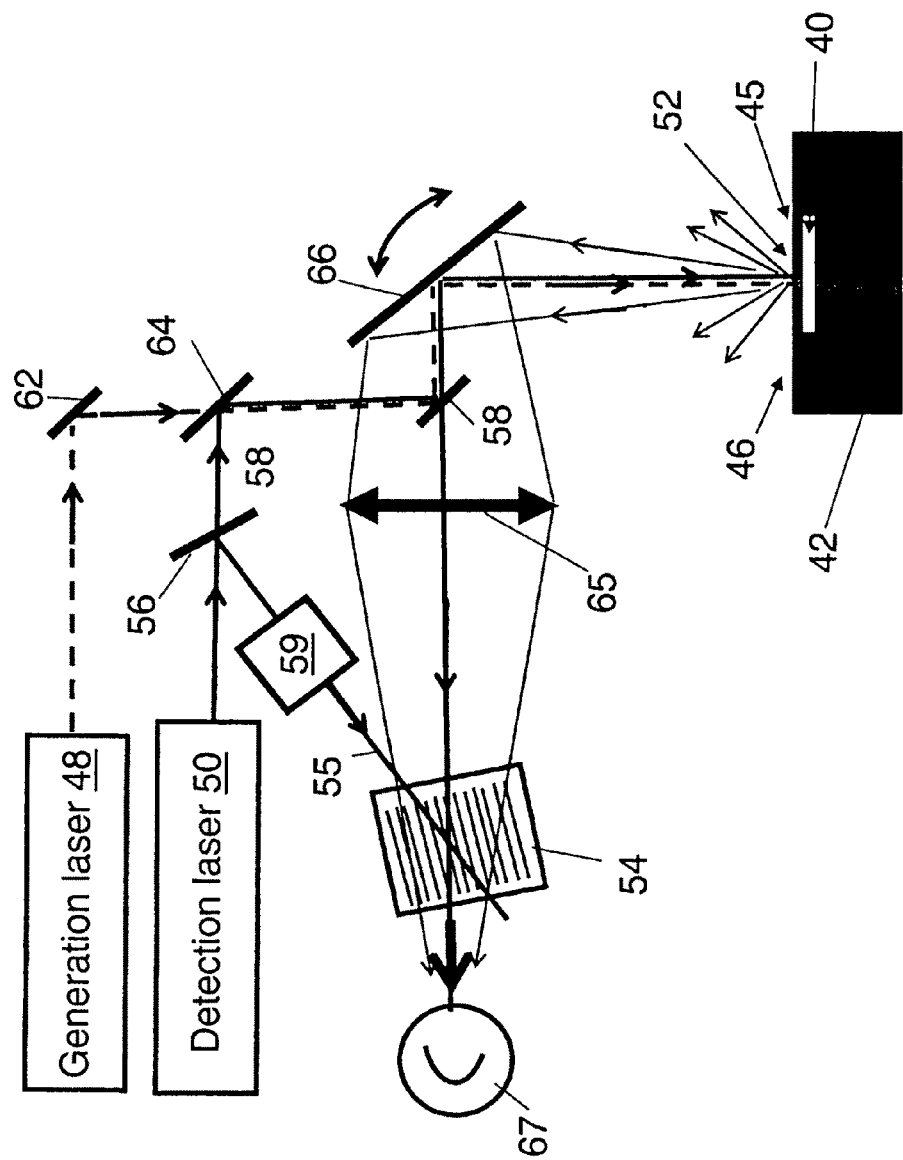

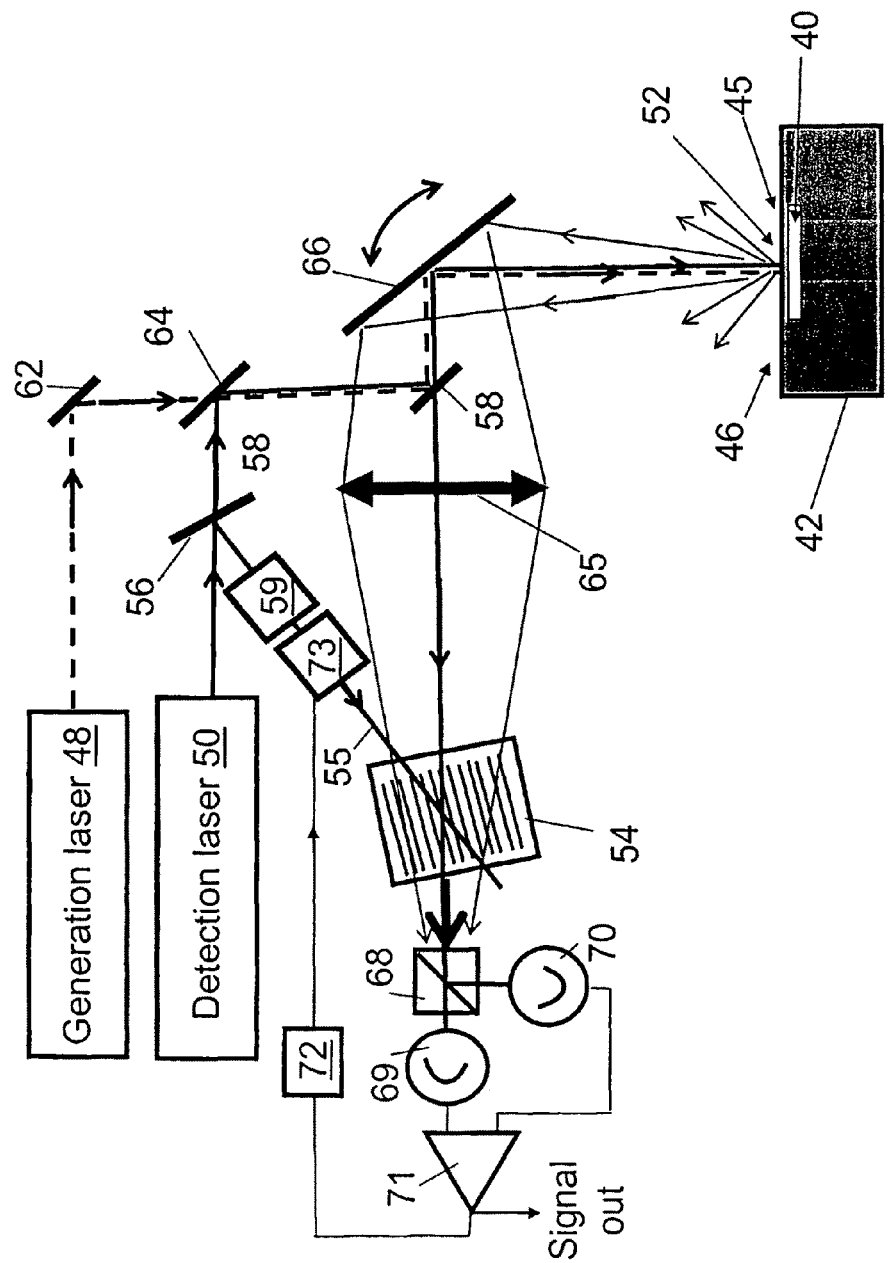

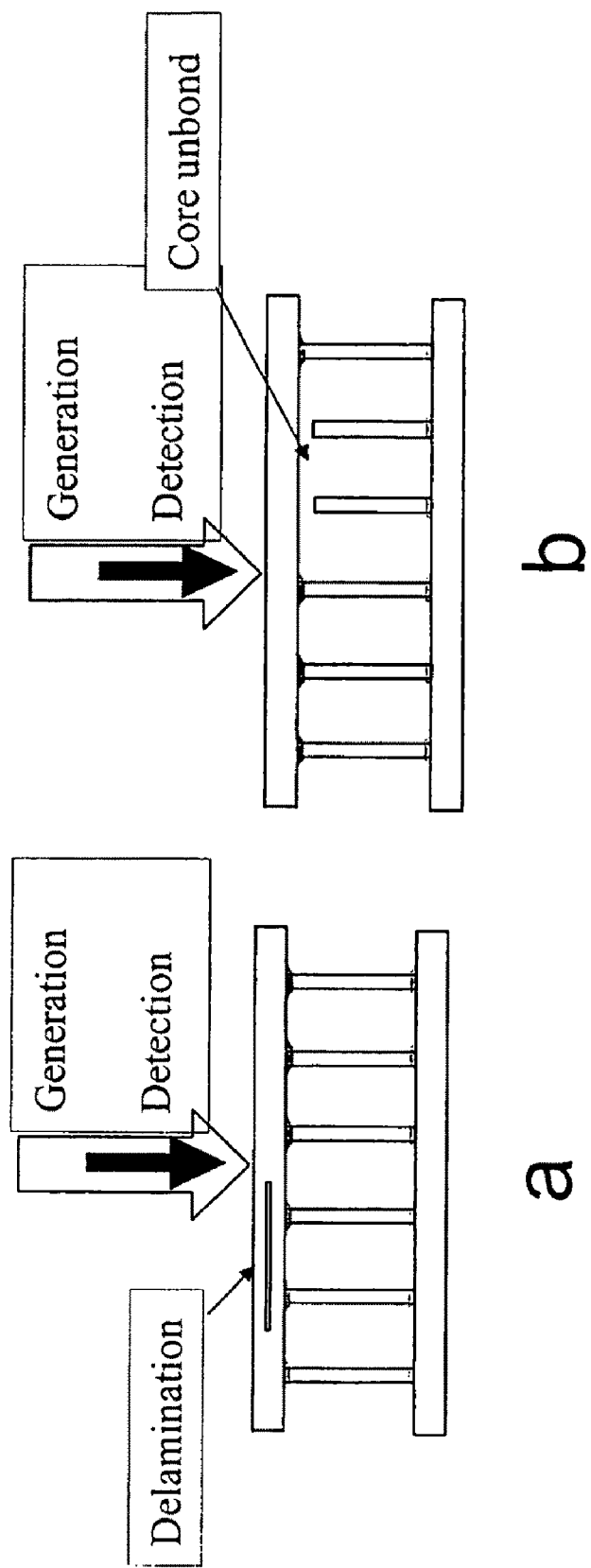

METHOD OF ASSESSING BOND INTEGRITY IN BONDED STRUCTURES

This application is a national stage entry of PCT/CA2007/000851 filed May 9, 2007. PCT/CA2007/000851 claims priority from provisional applications 60/799004 May 10, 2006 and 60/83761 Aug. 15, 2006.

FIELD OF THE INVENTION

The present invention relates in general to nondestructive testing of bonded structures, and in particular to a laser thermo-acoustic technique for assessing bond integrity.

BACKGROUND OF THE INVENTION

There are many bonded materials deployed in structural arrangements wherein the structural utility of the bonded material depends on a bond quality of the bonded material. In applications where the structural arrangements are critical, there is a need to evaluate the bond quality.

Honeycomb-structured materials allow fabrication of structures having reduced weight while keeping a very high stiffness. Such materials are particularly useful in the aeronautics and space industry. Honeycomb structured materials typically have two skins, and a core layer of ribs extending perpendicular to the skins to form hexagonal cells. The skins are usually laminates, such as e.g. carbon-epoxy laminates made of layers of carbon fibers in an epoxy resin. Two kinds of disbonds could occur in these structures, both resulting in a weakened structure: detachments between one skin and the ribs of the honeycomb; and delaminations within the skin. Probing honeycomb-structured components to find any disbond is important for assessing the quality of newly produced parts, and a condition of components during service. Similar structures also widely used in the aeronautics and space industries include a foam material intermediate the two skins instead of a honeycomb core layer.

Coated and laminated materials are other examples of materials for which bond assessment is important. Coatings are widely used on industrial material surfaces for protection against wear, oxidation, and corrosion or as thermal barriers, for example. Voids or detachments at the coating-substrate interface result in a fragile coating that could become detached, leaving the substrate unprotected and subjected to severe heat load, erosion, oxidation or corrosion. Coatings are made by different methods such as electroplating, thermal spray, painting, etc. or vacuum deposition for the thin and ultra thin multilayer coatings used by the microelectronics industry.

Very few techniques are known that can be applied to honeycomb or foam core-structured materials, particularly if the structure can only be interrogated from only one side. Known techniques use penetration of heat and/or acoustic waves (i.e. transmission ultrasonics) to detect disbond between a skin and the core. Difficulties arise because of limitations of penetration of acoustic and thermal waves through the bonded structure, and consequently there is very little change of properties, such as acoustic reflection or thermal conductivity, between a good bond and lack of bond. In the case of honeycombs this is partially due to the thinness of the ribs and in the case of foams to their very high porosity, which are the very properties that provide the strength and lightness that make the structures commercially valuable. Most of the techniques that have been developed to test bond integrity of coatings and the integrity of laminates from single side access cannot be applied reliably to honeycomb or foam core structured materials.

In practice, honeycomb and foam-core structures are presently inspected using transmission ultrasonics, i.e. with an emitting transducer on one side of the part and a receiving transducer on the other side (usually coupled with water jets on both sides). This technique, which requires access to both sides of the material, is possible at fabrication but usually not possible while assembled in a structure (such as in an airplane wing).

Regarding coatings, many coatings used in industry highly attenuate ultrasound. This is the case of thermal barrier coatings used on turbine blades and silicon carbide protective layers on carbon-carbon composites. The ultrasonic wave is strongly scattered and a very small coherent ultrasonic signal returns to the material surface in accordance with the pulse echo configuration. This large attenuation can be traced back to the size of material microstructure or porosity compared to the ultrasonic wavelength. For very thin coatings, attenuation does not damp out the coherent signal, but very high ultrasonic frequencies are required to resolve the ultrasonic echoes reflected back from the coating-substrate interface. Therefore all the existing ultrasonic techniques that require either contact or water coupling or non contact as in laser-ultrasonics have important limitations.

U.S. Pat. No. 4,752,140 to Cielo entitled "Pulsed dilatometric method and device for the detection of delaminations", proposes local heating and local interferometric detection. As explained by Cielo in U.S. Pat. No. 4,752,140 when laser heating is not uniform and is concentrated over an area smaller than the size of the detached zone, localized thermal stresses are produced that cause a stronger lifting and bending effect. As explained further by Cielo in various publications and in particular in "Thermoelastic Inspection of Layered Materials: Dynamic Analysis" (Materials Evaluation, vol. 43, pp. 1111-1116, 1985), the disbonded layer or skin can then be set into vibration like a membrane.

This latter approach proposed by Cielo has, however, several shortcomings which explain why it has not found practical use in industry despite having been disclosed more than 20 years ago. One is the fact that Cielo uses a Michelson-type interferometer (homodyne or heterodyne) for detection. When a high intensity light beam strikes a surface, typically the beam is reflected in all directions in an uneven manner defining a speckle pattern, each speckle of which having a high intensity. Homodyne or heterodyne interferometers are sensitive to the optical speckle produced by the roughness of the surface, which means that these interferometers have a maximum sensitivity to surface displacement when only one speckle of the light scattered by the surface is collected. This is because each speckle of light returning from the surface effectively is a separate beam having its own respective random phase offset and random amplitude, and consequently, if multiple speckles are gathered for use in such an interferometer, each pair of beams (speckles as well as the reference beam) produces a separate interference pattern, all of which interference patterns are superimposed, resulting in a sharply reduced sensitivity of the measurement.

Since the intensity of the collected speckle typically varies strongly from one interrogation location on the surface to the other, the sensitivity of the device also strongly varies from one location to the other. Accordingly, scanning a part to get an image of the adhesion integrity of the structured material is not very practical.

This technique can be applied to a honeycomb structure with specially polished aluminum skins for which the light reflected off the surface is nearly speckle-free. Such cases in practice never occur; skins are usually made not of aluminum but of polymer-matrix fiber reinforced laminates. It would be unpractical and too onerous to apply a special coating or paint which has a sufficiently smooth surface to give speckle-free reflection.

There therefore remains a need for a nondestructive technique for detecting a disbond in a bonded structure, such as a coated, honeycomb or foam-core structured material, where the disbond forms a membrane at a top layer of the bonded structure.

SUMMARY OF THE INVENTION

In one aspect of the invention, there is provided a method of assessing bond integrity at a region in a bonded material comprising: producing transient heating in the region, the transient heating adapted to induce a membrane vibration within the bonded material if the region overlies a disbond in the bonded material, the vibration having a vibration period; and detecting any vibration at the surface using a large etendue interferometer with a response time sufficiently short to adapt to ambient vibrations and speckle changes, and substantially longer than the vibration period.

In another aspect of the invention, there is provided a method of detecting disbonds in a bonded material at a spot on the surface of the bonded material, the method comprising: subjecting the spot to a first laser pulse having a wavelength and an intensity to produce transient heating at the spot, the spot having an area smaller than an expected dimension of a disbond; the transient heating producing by thermoelastic effect a displacement and a vibration of a membrane between the disbond and surface of the bonded material, the vibration having a vibration period; illuminating the disbonded area by a second laser pulse substantially longer than the vibration period; receiving scattered or reflected light from the second laser pulse in a large etendue interferometer with a response time sufficiently short to adapt to ambient vibrations and speckle changes, and substantially longer than the vibration period; and, producing with the interferometer a signal indicative of the displacement and/or vibration of the delaminated and/or disbanded area.

Transient and local heating, e.g. heating over an area smaller than the disbanded area, by a pulsed laser followed by interferometric interrogation of the surface deformation by another laser provides an approach to detecting disbonds. The area subjected to the first laser pulse preferably has a diameter of less than half of the diameter of the disbonded area. The approach may employ a photorefractive interferometer or a similar interferometric detection device that is not sensitive to optical speckle but is sensitive to acoustic frequencies, preferably in a range of from about 1 kHz to about 1 MHz.

The material may be a layered and/or composite bonded structure, for example, a honeycomb structure, a structure with a foam core, a coating on a solid, a laminate etc. On honeycomb structures and on foam core structures, if a sufficiently short generation pulse is used, the approach can also exploit ultrasonic waves that are generated through the membrane to get a more thorough and reliable inspection by distinguishing delaminations within the skin from detachments of the skin from the ribs. Furthermore, on laminates and in structured materials that may develop disbonds at different depths, the use of a short pulse allows for determination of a depth of the disbond using a time between the reverberating ultrasonic echoes. Thus, the present method is particularly useful for analyzing honeycomb and foam core structures.

In the case of honeycomb and foam core structures, disbonds are either detected at the top skin, upon which the laser pulses impinge, or the bottom skin. In some materials, this bottom skin could be sandwiched between two honeycombs or two foam core structures.

The interferometer may be based on two-wave mixing in a photorefractive material, based on photoelectromotive force, based on polarization self-modulation effect, or based on an array of interferometers followed by electronic processing.

An image of the disbanded area may be obtained by scanning the lasers or the structure. The scan may be momentarily stopped for interrogating the structure. The scan may be continuous. In this case, Doppler shift may be compensated by frequency tracking.

Disbonds may be detected by monitoring harmonics or higher order modes of the vibration of the disbanded area, and these may be more readily detected at a periphery of the disbanded area.

The first laser pulse preferably has a pulse duration short enough to produce ultrasonic echoes reverberating within the disbonded area. Location and depth of the disbanded area can be determined. The pulse period of the first laser pulse may be less than 1 µs, for example in a range of about 50 ns to about 200 ns. The first laser pulse may be sufficiently powerful to produce detachment of any stick bonds present.

The second laser pulse has a pulse duration longer than the vibration period of the membrane. The pulse duration of the second laser pulse is preferably about twice or greater than the vibration period.

The response time of the interferometer is sufficiently short to adapt to ambient vibrations and speckle changes and sufficiently longer than the vibration period to produce a signal indicative of the membrane vibration. The response time is preferably about twice or greater than the vibration period to be measured.

BRIEF DESCRIPTION OF THE DRAWINGS

In order that the invention may be more clearly understood, embodiments thereof will now be described in detail by way of example, with reference to the accompanying drawings, in which:

FIG. 3a is a schematic diagram of an apparatus in accordance with an embodiment of the present invention;

FIG. 3b is a schematic diagram of an apparatus in accordance with an embodiment of the present invention having frequency tracking equipment;

FIGS. 4a,b are a schematic side views of a thin section of a honeycomb structure showing two kinds of disbonds: a delamination within a skin and a detached core;

DETAILED DESCRIPTION OF THE INVENTION

A non-destructive test for disbond of a structured material is provided based on acoustic excitation of a membrane formed at a surface of the structured material by the disbond. Detection of the acoustic excitation is performed by a large etendue interferometer.

Theory of Membrane Vibration

Modes of the vibration induced in a membrane formed by a disbond by transient heating in a material are determined by the material's elastic properties, its geometrical shape and the thickness of the membrane. In particular, for honeycomb and foam core structured materials, the thickness can be approximated to be the skin thickness. Also for honeycombs, it should be noted that each cell produces a vibrating membrane that can be set into vibration if the heating zone (i.e. laser spot) is smaller than the cell size.

Figure 1:
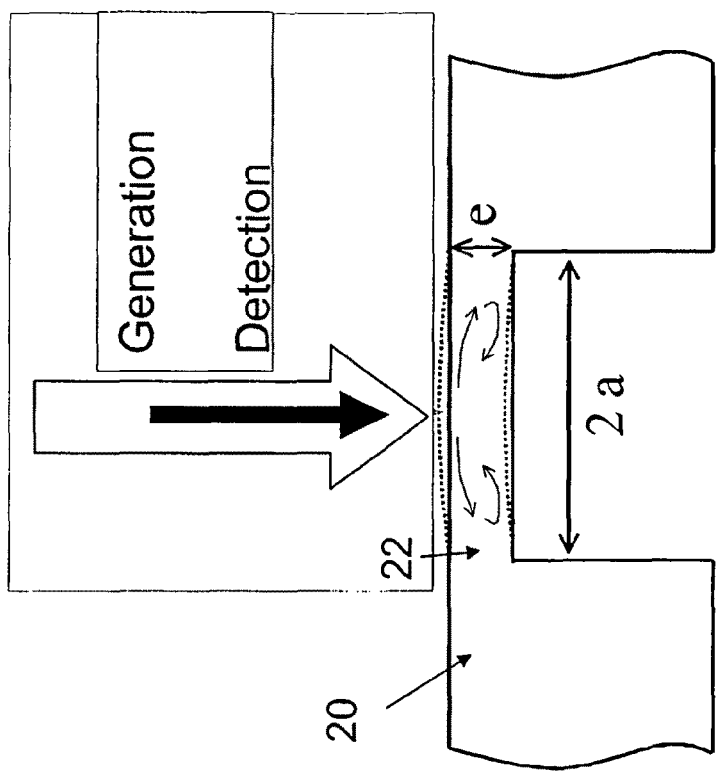
FIG. 1 is a schematic diagram of thermal excitation and flexural vibration of a clamped membrane and optical detection.

FIG. 1 is a schematic cross-sectional illustration of a theoretical clamped circular plate 20 having a membrane 22 surrounded radially by a supporting member. For such a circular membrane 22, the fundamental vibration frequency $f_1$ is given by equation 1:

$$f_1 = 0.47 \frac{e}{a^2} \sqrt{\frac{Y}{\rho(1-v^2)}} \quad (1)$$

where e is the thickness of the membrane, a its radius, $\rho$ is the mass density, Y is the Young's modulus and $v$ is Poisson's ratio of the material. While this idealized example with a circular uniform membrane having perfect clamping along the circumference etc. and having no interference from a substrate below does not correspond accurately to a practical disbond application, it provides a basis for determining a range of fundamental frequencies expected of a bonded surface having a disbond of a given size.

It is known that a membrane can vibrate at higher frequencies associated to higher order modes. Distribution of the vibration amplitude of these modes across the membrane surface depends upon the shape of the membrane.

Figure 2:
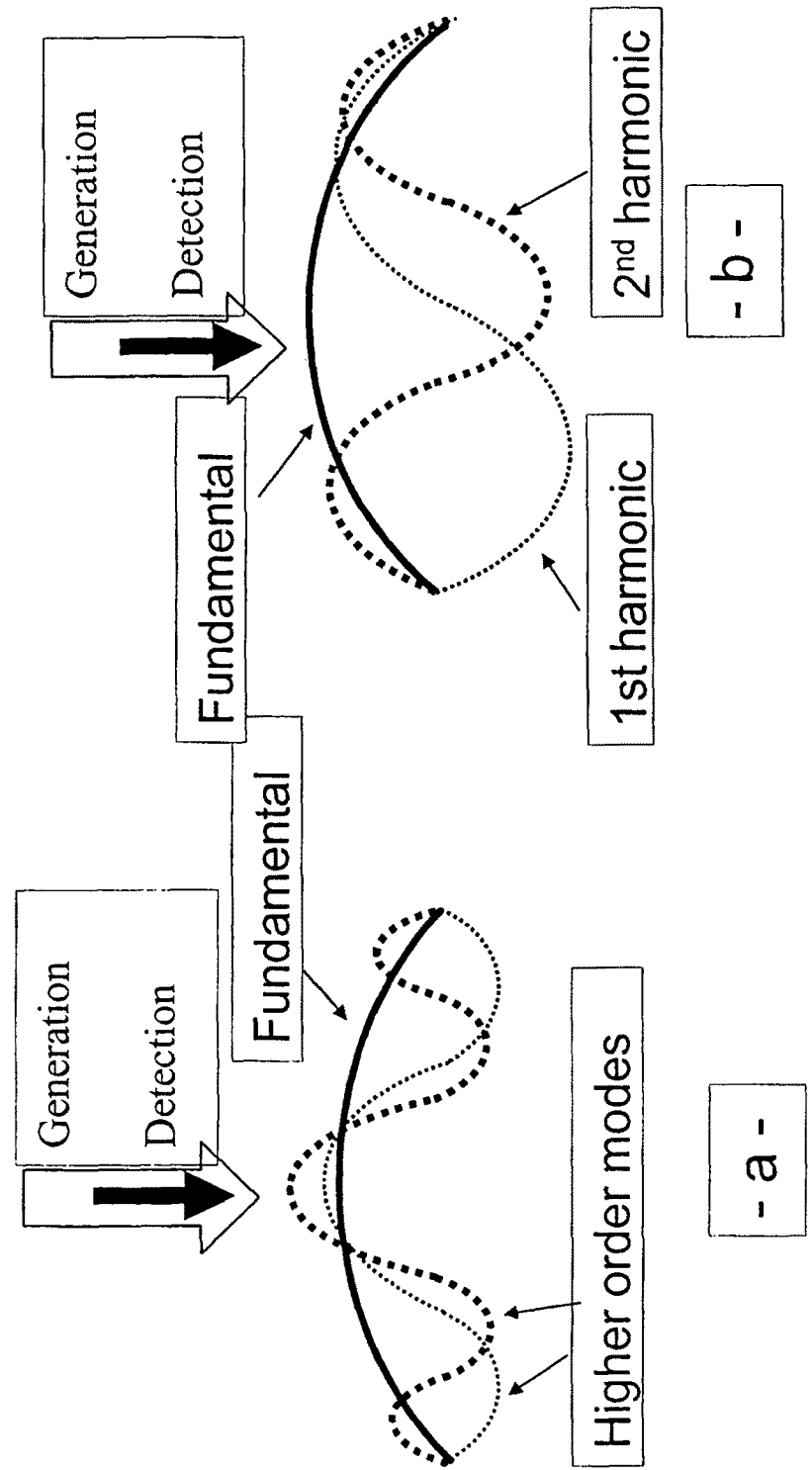
FIG. 2 is a schematic diagram of excitation and detection of higher harmonics of a vibrating membrane.

FIG. 2*a* is a schematic illustration of the vibration of the fundamental mode and two higher order modes of vibration of a circular membrane. Only modes with radial symmetry are shown for simplicity. There are also other modes with azimuthal dependence.

FIG. 2*b* is another schematic illustration of the lowest order modes of an elongated rectangular membrane. In practice, disbonds often have irregular shapes and their vibration modes cannot be as easily predicted. However it can be said that the fundamental vibration mode will have a maximum somewhere in the middle of the disbond whereas higher modes will display several maxima with at least one close to the edge of the disbond and will be of higher frequency than the fundamental vibration.

Thermoelastic Excitation

Transient heating by a pulsed laser (generation laser) produces thermal expansion at the surface of the membrane or near its surface and induces a stress, which in turn makes the membrane to bulge and then to vibrate. In order to have strong lifting it is advantageous to deposit the laser energy over a sufficiently small spot to impart a wide band of frequencies into the membrane, and the properties of the membrane will determine which frequencies lead to resonance.

The basis for detection used in accordance with the invention is membrane resonance. For a given membrane shape and size, the vibration modes that will be excited depend upon the dimension of the excitation laser beam and its location. When the excitation is at a middle of the membrane, the fundamental mode is preferentially excited. When the excitation beam has a sufficiently small diameter (e.g. less than the fourth of the membrane size) and located near the edge of the disbond higher order modes are preferentially excited. It should be noted that these higher order modes have higher resonance frequencies than the fundamental, and therefore can be detected with a detection apparatus with a higher low frequency cut-off. Only a perimeter of the disbond may therefore be detected.

Accordingly the transient heating does two different things, it provides a lifting of the membrane from the substrate, and it sets the membrane in vibration.

Although in practice a disbond could have an irregular shape, an order of magnitude of its fundamental resonance frequency can be obtained by using equation 1 with an effective radius. For example, for a detachment of a carbon epoxy skin thickness e=0.9 mm and having an effective radius a=10 mm, assuming a density, a Young's modulus and a Poisson's ratio of 2000 $Kg/m^3$, 150 GPa and 0.2, respectively, equation 1 yields a fundamental vibration frequency of 37 kHz, which corresponds to a vibration period of about 27 μs. For a larger disbond or thinner skin, this frequency would be even lower.

Interferometric Detection

Preferably a photorefractive interferometer or similar interferometric detection device that collects light from multiple speckles (i.e. has a large etendue) and has been developed for the detection of ultrasound is used. A photorefractive interferometer is based on the photorefractive effect in an optically nonlinear material. Different schemes have been proposed based on the Two-Wave Mixing [U.S. Pat. No. 5,131,748 by Monchalin and Ing and U.S. Pat. No. 5,680,212 by Blouin, Delaye, Drolet, Monchalin, Roosen], or the polarization self-modulation effect [Kamshilin].

Basically all of these methods involve a beam splitter receiving an output from a coherent light source such as a detection laser, and dividing the beam into an interrogation beam for striking the surface of the bonded material, and a pump beam directed onto a photorefractive material. The interrogation beam is then reflected or scattered by the surface to be finally sent onto the photorefractive material where it interferes with the pump beam and produces by the photorefractive effect a transient hologram or index of refraction grating or photorefractive grating. Once the transient hologram/grating is produced, the pump beam is diffracted by it to produce a reference beam during a detection phase of the interferometer. The reference beam interferes with the transmitted interrogation beam to produce an interference pattern detected at a photodetector. This photodetector provides an electrical signal representative of the surface vibration. Alternatively, instead of using a photodetector, the material can be equipped with electrodes and a signal representative of the surface vibration can be obtained by detecting the photoelectromotive force, as is explained, for example by [Petrov].

A response time ô of the interferometer is a time it takes for a photorefractive grating to build up within the photorefractive material, and then to produce the interference . For example, if two-wave mixing is used, the response time is the time required by the interferometer to write a photorefractive hologram and to build up its sensitivity at the beginning of each optical detection pulse.

Photorefractive interferometers can be operated with a slow enough response time to capture low frequency motions of a membrane by reducing the pump beam intensity, as explained by [BlouDel, Kot]. According to the carbon epoxy example above, a pulse duration of the detection laser of about 100 µs is sufficiently long to capture at least a few cycles of the vibrations. Such a long pulse is not usually used to detect ultrasound.

With proper tuning, other large etendue interferometers based on photorefractive or photoactive materials can be used, instead of the TWM-based phase interferometer. It is also possible to use the newly reported interferometric technique by Pouet [Pouet]. This scheme does not use any photorefractive or photoactive material but uses instead an array of quadrature interferometers and detectors. In this case ô is determined by electronics filtering which is used before processing the signal.

Accordingly, in accordance with one embodiment of the invention, surface displacement of the bonded structure is measured with a two-wave mixing photorefractive interferometer which collects the scattered light from a plurality of speckles. In order to make a sensitive measurement, the response time $\tau$ should be longer than the vibration period T so that the photorefractive grating is quasi-stationary during the vibration period. For example if the period of vibration T is about 10 µs (membrane vibration frequency is about 100 kHz), $\tau$ is more than about 10 µs, e.g. about 20 µs (corresponding to a cutoff frequency $1/(2\pi\tau)=10$ kHz. On the other hand, if ô is too long, the interferometer will be highly sensitive to ambient vibrations, making it inadequate for inspection in many industrial environments. Therefore the response time $\tau$, which can be controlled by the photorefractive optical pump beam power extracted from the detection laser, should not be too long in order to provide continuous adaptation of the photorefractive grating to ambient vibration. Since ambient vibrations are typically strong below 1 kHz, the above example shows, as we have found, that it is possible to satisfy both requirements.

For example, consider a laser repetition rate of 500 Hz, having a period of 2 ms. More than 1 ms may be used for interrogation, permitting a very long response time (corresponding to relatively weak pump power sent onto the photorefractive material). In this case, the response time $\tau$ could be substantially as long as desired permitting detection of larger and thinner membranes, bounded only by the detection laser pulse duration $t_L$ and the desire to avoid noise which is increasingly problematic at lower frequencies to minimize the effects of ambient vibrations.

It will be appreciated that higher laser repetition rates are equally possible, and that generally the highest repetition rates will be used to expedite a high resolution C-scan image in a minimum acquisition time. The tradeoff to higher repetition rates is the shorter response time of the large etendue interferometer, and the higher low frequency cut-off corresponding to a lowest frequency motion of the membrane that can be detected.

A scan of the surface can be obtained by moving the interrogation beam and generation beam with respect to the surface and making respective measurements at each point when the motion of the interrogation and generation beams is stopped. This implementation puts more severe requirements on the mechanics of scanning equipment and control thereof, since mechanical parts have to be repetitively put into motion and stopped, but it permits an arbitrarily long time for the interferometer to adapt to the speckle.

If it is desirable to continuously scan the surface, the speckle pattern will change continuously, and consequently the response time of the interferometer will have to be sufficiently fast to adapt itself to the changing speckle pattern. Furthermore, unless the interrogation beam scanning across the surface of the bonded structure makes a right angle, a Doppler shift will take place and diminish very significantly the sensitivity of the photorefractive interferometer.

The response time ô must be made shorter in order to provide adaptation to the speckle variation and Doppler shift. A shorter $\tau$ results in a higher interferometer cutoff frequency which then places a lower limit on the vibration frequency and an upper limit on the size of membrane that can be detected (or a lower limit on the thickness).

If the membranes only vibrated at a fundamental frequency, large surface area membranes would be missed. Given the greater importance of detecting larger disbonds, and the undesirability of multiple scans, this would make the setup undesirable. The detection of higher modes of vibration than the fundamental membrane vibration permits detection of larger surface area membranes. It is applicable to the stop scanning implementations as well to the continuous scanning ones. These higher order vibration modes are typically most effectively excited at the edge of the disbond. When the excitation is at the middle of the membrane, the fundamental mode is preferentially excited and the disbond may not be detected as its frequency may be too low in comparison with the low frequency cut-off of the photorefractive interferometer. Therefore in this case the disbond will give an indication only along its perimeter whereas its central part will show none.

Furthermore, if the continuous scanning is performed at a significant angle to the surface (e.g. 45°), and at a significant rate (e.g. at a tangential velocity of V=1 m/s), the Doppler shift $(2V/\lambda)$ will be about 2 MHz for the wavelength $\lambda=1$ µm. To compensate for such a shift, the response time could made very short (e.g. about 100 ns), which may not be feasible on one hand, and would restrict the interferometer to the detection of very small disbonds on the other hand.

In such a case, one can use the frequency compensation scheme described in U.S. Pat. No. 6,700,666 by Blouin, Drolet, Monchalin and Padioleau, which makes the interferometer operate as if the beam is at normal incidence by incorporation of a velocity sensing arrangement and an acousto-optic shifter for frequency adjustment of one or both of the interrogation and pump beams, as explained therein.

Therefore, only the normal incidence case has to be considered, if such compensation scheme is used. If the surface is essentially perpendicular to the beam, there is essentially no Doppler effect and $\tau$ typically hundreds of times larger can be used, e.g. τ=20 μs, which means, using data from the example above, that membranes as large as about 15 mm can be detected. However to reliably detect larger disbonds, the scanning speed will have to be reduced or one should rely on the detection of higher vibration modes as indicated above.

Regarding the use of the interferometer scheme reported by Pouet, the Doppler shift of the collected beam while scanning results in a large modulation signal at the Doppler frequency on the detectors. This parasitic signal should then be removed by electronic filtering which also remove the sensitivity of the device to phase modulation below the cut-off frequency of the filter. As we have seen above for the photorefractive interferometer, this will result in detection of very small disbonds but a frequency compensation scheme (not disclosed by Pouet) can be implemented which reduces the problem to normal scanning. In conclusion, since this system uses high pass filtering to eliminate vibration effects and speckle change signals (i.e. it has also a response time ô), it has the same limitations regarding the detection of large disbonds and the same warnings and solutions presented above for photorefractive interferometers apply.

Another method for Doppler shift compensation that could be used on a sufficiently reflecting material surface is to use two detection laser spots impinging on neighboring points of the surface. If the separation is large enough so that one laser spot is subject to membrane vibration and the other laser spot is not, assuming also that the surface is locally essentially planar, then both beams are equally Doppler shifted, but only one is phase modulated by the vibration of the detached area. The light collected back from the spot is used for the interrogation beam of the interferometer while the light from the other spot is used for the pump beam.

Apparatus

FIG. 3a is a schematic illustration of an apparatus for detecting a disbond 40 in a bonded structure 42 that produces a membrane 45 at a surface 46 of the bonded structure 42. The apparatus includes a generation laser 48 for generating acoustic vibrations in a membrane, if extant, and a detection laser 50 for detecting the acoustic vibrations both on a same side of the bonded structure 42.

The generation laser 48 produces a pulse having a pulse duration, wavelength and intensity to produce transient heating of the surface 46, such that if the pulse strikes the membrane 45, the membrane is lifted from the structure below and made to oscillate by thermoelastic effect. To this end, a diameter of a spot 52 of the generation laser at the surface 46 is less than an area of the membrane size by a factor of 2 or more, and the generation laser is a short pulse laser. The generation laser 48 is preferably a short pulse laser and the wavelength and intensity may be selected so that the transient heating is entirely, or substantially within the thermoelastic regime to avoid surface damage.

The detection laser 50 may be a continuous laser or a pulsed laser. As only a limited interval provides useful information, and higher power and sensitivity can be obtained with a pulsed laser, a pulse laser is preferably employed. In addition, since the laser energy may be partly absorbed by the tested part, a pulsed laser limits the heat load deposited on the tested part. The pulse duration is chosen to capture at least a few cycles of the membrane vibration induced by the generation pulse (typically about one ms or less in the numerical examples given).

The detection laser 50 is associated with a large etendue interferometer for detecting surface displacement of the bonded structure 42 at or adjacent the generation laser spot 52. While the interferometer shown uses a two-wave mixing photorefractive material 54, it will be appreciated that any interferometer that can collect light from multiple speckles (i.e. that has multiple components having different phase offsets), and is adapted to detecting surface displacements of the magnitude and frequency produced by the generation laser 48 can be used. In particular those interferometers listed above are practical alternatives.

The beam from the detection laser 50 is divided by a beam splitter 56 into a pump beam 55, and an interrogation beam 58. The interrogation beam 58 is directed onto the surface 46 of the bonded structure, where it is scattered. The pump beam 55, in accordance with the illustrated embodiment is subjected to an optical power controller 59 to control its power to ensure a desired response time of the interferometer, although this power control could be provided in other ways known in the art.

A beam from the generation laser 48 and the interrogation beam 58 may be brought together (substantially overlapping, and substantially parallel) in any manner known in the art, for example using a reflector 62, and a dichroic beam splitter 64, as shown, although other methods are equally applicable in different embodiments. The two substantially overlapping beams are jointly directed onto the surface 46 by mirror 66. Mirror 66 may be a scanning mirror or other beam moving device adapted to move the spot 52 across the surface 46, in a manner known in the art. Alternatively the sample could be moved to produce the scanning. Scattered light is collected by a large lens 65 (or mirror) which transmits it to the photorefractive material 54 where it produces a photorefractive grating. Finally a signal representative of the surface motion is produced by the interference of the transmitted scattered light and the beam from the pump beam diffracted by the photorefractive grating, which is detected at a photodetector 67.

The pulse duration $t_L$ of the detection laser is longer than the vibration period of the membrane T (2T and beyond). For example, $t_L$ could be 200 μs, and, in this case, is well adapted to detect detachments characterized by a period T=50 μs and shorter. Since repetition rates in the range of 100 Hz to 1 kHz are considered, this pulse length is also properly shorter than the interval between pulses. The detection spot size is about the same as generation, and in any case much less than d, otherwise there will be some integration over the vibrating membrane surface resulting in a lower signal, since the membrane is clamped at its edges FIG. 3b shows an embodiment applicable to the continuous scanning mode and providing Doppler shift compensation. The Doppler shift compensation is based on the scheme described in U.S. Pat. No. 6,700,666. The configuration is the same as in FIG. 3a except for several elements added for providing Doppler frequency tracking and compensation. Descriptions of corresponding features from FIG. 3a are not repeated.

As shown in FIG. 3b, there are two photodetectors 69 and 70 receiving two signals from polarizing beam splitter 68 at the output of the photorefractive interferometer. These photodetectors feed differential amplifier 71. As explained in U.S. Pat. No. 6,700,666 the low frequency signal at the output of the differential amplifier 71 is proportional to the frequency difference between the pump beam and the Doppler frequency shifted interrogation beam. This signal is sent to a Voltage Controlled Oscillator 72, that drives an acousto-optic shifter 73 in such a way that the frequency of the pump beam incident on the photorefractive material follows the frequency of the interrogation beam. As a consequence, the Doppler effect is cancelled as if the interrogation beam was perpendicular to the surface. The membrane vibration signal and the ultrasonic signal are also picked up at the output of the differential amplifier 71 by high pass filtering.

A second shortcoming with the technique according to Cielo described above occurs with honeycombs or foam core structure. The vibration frequency of a detached membrane is a function of both the thickness and the effective size of the membrane. Also disbonds do not have generally well defined shapes, so in general, it is not readily possible to know whether a detected vibration is attributable to a delamination within the skin or to a detachment of the skin from the honeycomb or the foam core.

The second shortcoming of Cielo mentioned above may be circumvented by using a sufficiently short generation pulse. Cielo uses long pulses above 1 µs. Such long pulses can only generate ultrasound with a long wavelength. Typically, 1 µs, which is the shortest pulse mentioned by Cielo, corresponds in polymer matrix composites to a spatial length of the pulse of about 3 mm (velocity in the range of 3 mm/µs). Therefore delaminations between plies (a ply thickness is typically 100 to 200 µm) cannot be detected since the ultrasonic echoes are not separated. But using shorter pulses, e.g. about 100 ns, these echoes can be separated and are detected due to the large bandwidth of the photorefractive interferometer. As it is well known, from these echoes one can extract the membrane thickness and therefore the depth of the delamination or disbond. In particular for a honeycomb or foam core structure, this allows to distinguish between a delamination within the skin and skin detachment from the core. However, too short of a pulse duration may damage the material. Some damage may be acceptable for the benefit of producing a stronger surface stress, which in turn causes a larger bending and lifting of the disbonded layer or skin.

Advantageously the same detection laser can be used to detect low frequency membrane vibration and high frequency ultrasonic vibrations. This can be accomplished by applying respective filters to two copies of the surface displacement signal from the interferometer and analyzing separately the resulting signals.

Strong laser excitation, which may cause some surface damage, may be used in cases where the layer or skin is not completely disbanded, but attached through a weak bond, often called a stick bond. Such stick bonds have very weak strength and are very dangerous flaws that could lead to catastrophic failure of a whole structure. They are not usually detectable by ultrasonic techniques since they transmit ultrasound well. However, using the present method, the bulging caused by localized laser heating may be sufficient to open the bond, thereby producing membrane vibration and making such stick bonds detectable.

EXAMPLE 1

Honeycomb Carbon Epoxy Test Sample

Figure 5:
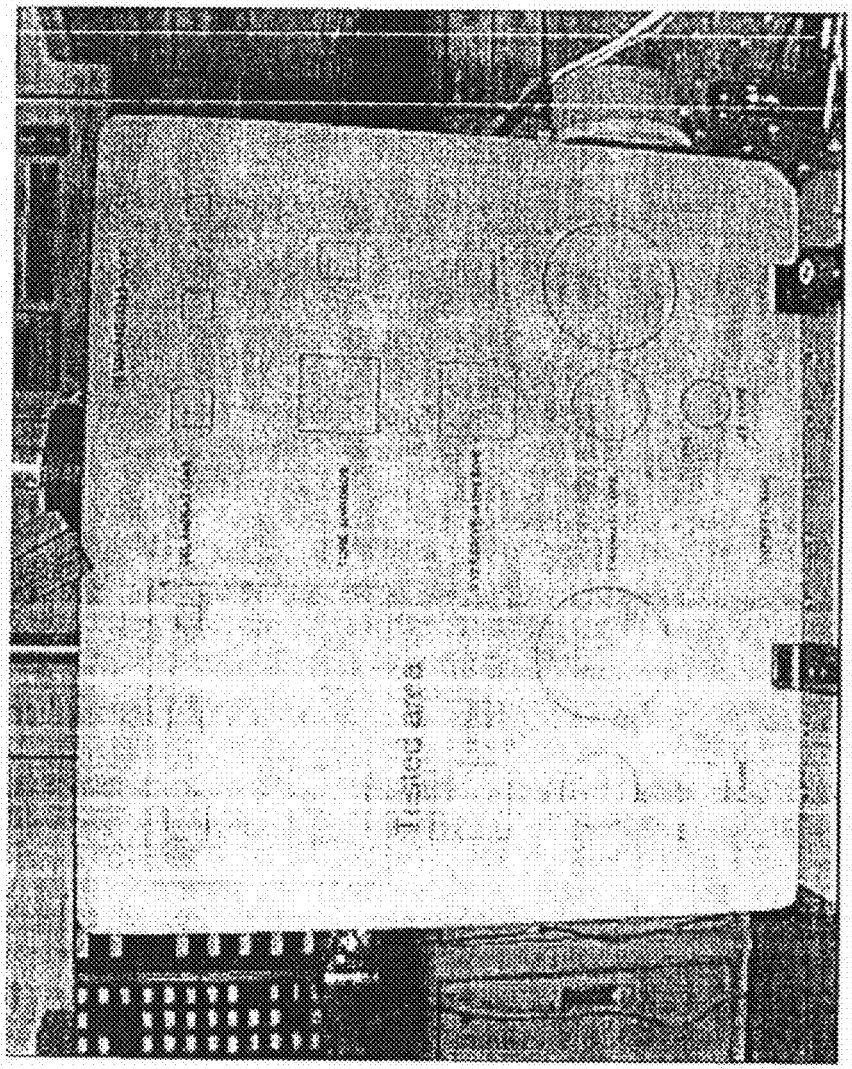
FIG. 5 is photograph of a honeycomb carbon epoxy test sample with an 11 cm×9 cm rectangular disbond test area.

Example 1 is an application to a carbon epoxy honeycomb structure with artificially produced delaminations in the skin, and skin-core detachments. A schematic illustration of the location of the defects is shown in FIG. 4, and a picture of the test sample is shown in FIG. 5.

The experimental setup as shown in FIG. 3a is used. The generation laser employed is a $CO_2$ TEA laser which delivers pulses of about 100 mJ energy and 120 ns duration at 10.6 µm wavelength makes the detached area lift up and vibrate like a membrane clamped at its edges. It also generates ultrasonic waves. The excitation mechanism in this case is purely thermoelastic, and non-damaging. The detection laser is a pulsed single frequency Nd:YAG laser which delivers pulses of about 50 mJ energy and 65 µs duration at 1.064 µm wavelength, and the laser detects both the vibration and ultrasound echoes. The detection laser light scattered off the surface of the inspected part is sent to a TWM interferometer based on an InP:Fe photorefractive crystal under an applied voltage. Both lasers were scanned on the part to be inspected using a 1-mm step size along X and Y-axis. The scanning system was of the stop type. The beams were collinear and overlapped so that generation and detection were performed at the same location. The beams were scanned over the area indicated in FIG. 5 at a standoff distance of 1.4 m from the scanning mirror.

Vibration frequencies are expected to be in the 20 kHz to 1 MHz range depending on the physical and mechanical properties of the material and detachment dimensions. The low frequency cutoff of the TWM phase interferometer was adjusted to 15 kHz, which means a grating build up time of about 10 µs, by properly setting the optical pump power of the TWM phase interferometer. The surface displacement signal measured by the interferometer was then processed in the Fourier domain to identify the value of the vibration frequencies of the detached areas. A replica of the same signal was also high pass filtered to display the ultrasonic echoes, permitting a determination of a thickness of the membrane.

Figure 6:
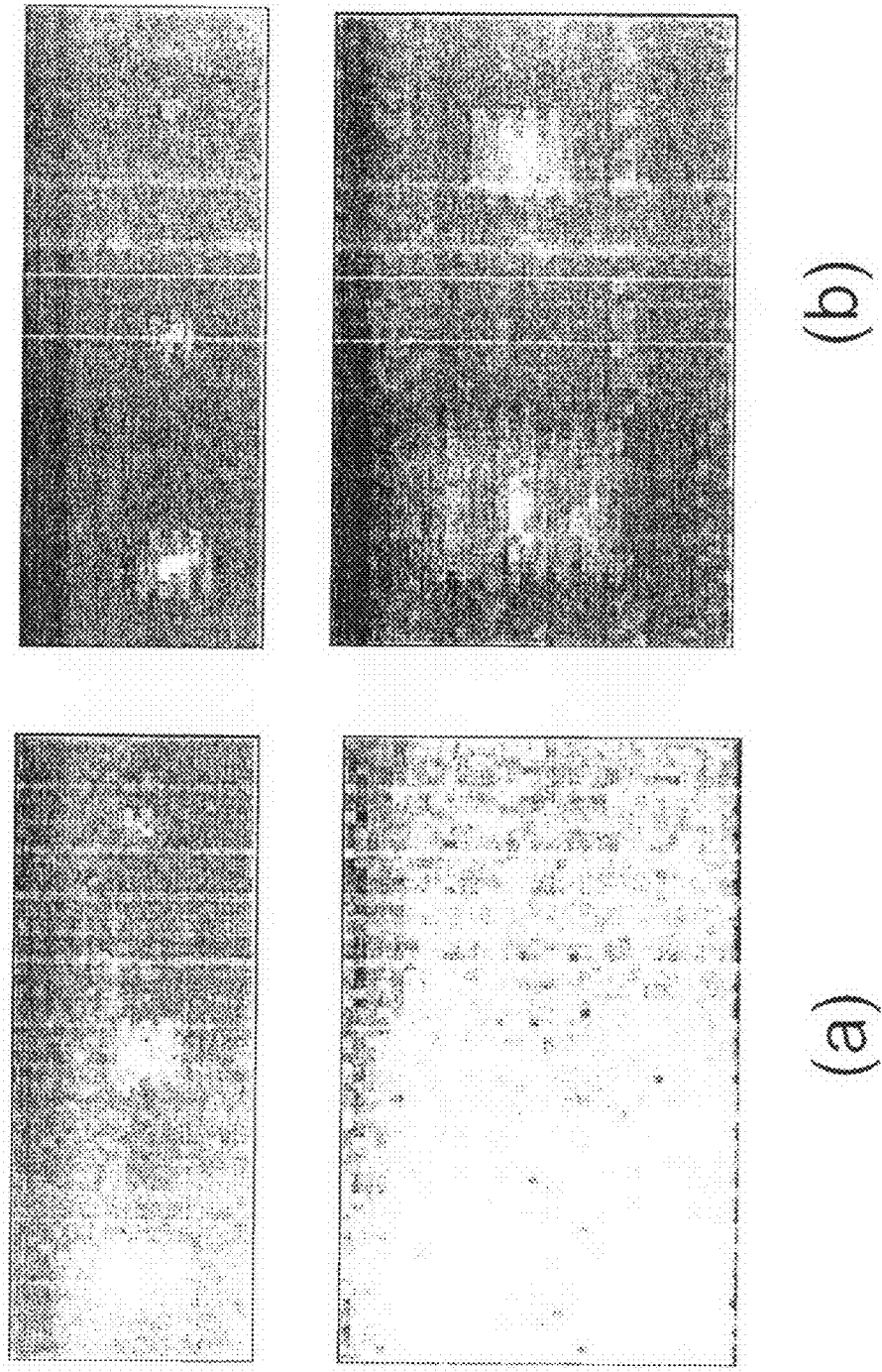
FIG. 6a is a C-scan plot of the maximum amplitude after high pass filtering of the disbond test area shown in FIG. 5 in accordance with the laser-ultrasonic pulse echo method.
FIG. 6b is a C-scan plot of the maximum amplitude of the low frequency (membrane vibration) technique, in accordance with an embodiment of the invention.

FIG. 6a shows a C-scan of the inspected area obtained by filtering the signal with a 1.6 MHz cutoff high pass electronic filter and by plotting the maximum amplitude of the ultrasonic echoes in the first 17 µs of the signal. As seen in this image, the delaminations within the skin are well detected but not the disbond between the skin and the honeycomb. The detachment of the skin and honeycomb are not detectable by the ultrasonic echo method because at the interface between the skin and the honeycomb core, substantially all the acoustic wave is reflected regardless of the state of attachment or detachment. From the time of arrival of the first echo or the reverberation time between echoes, the depth of the delamination can be readily determined, as is well known in the art.

FIG. 6b shows the plot of the maximum amplitude of the signal in a much longer time gate (140 µs) without high pass filtering. In this case the low frequency membrane vibration is dominant. As seen in this image both delaminations within the skin and disbonds between the skin and the honeycomb are detected. As mentioned above, it is not straightforward to determine the depth of a disbond from the vibration data alone. This example illustrates how this can be obtained by choosing a sufficiently short excitation pulse that produces both ultrasonic echoes and membrane vibration.

Another interesting way to present the data is to plot in a C-scan the frequency of the peak amplitude of the signal Fourier Transform. These frequencies are related to the size of the detachments. The higher the frequency: the smaller the size. In the C-scan of FIG. 7, we plot the frequencies of the maximum amplitude in the Fourier domain within the spectral interval ranging from 25 kHz to 120 kHz. FIG. 8 shows the distribution of these vibration frequencies along the white dotted line passing through detached areas. The detachment on the right side has a larger vibration frequency than the others, which is expected since its size is smaller.

Figure 7:
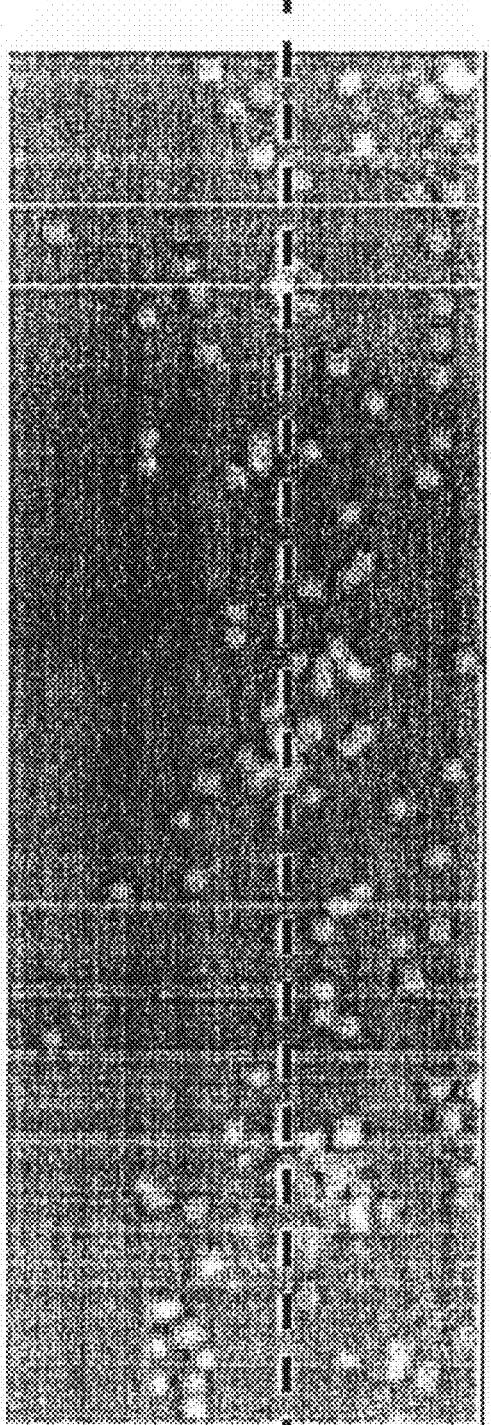
FIG. 7 is a C-scan plot of principle vibration frequency over 3 delaminations of the disbond test area.
Figure 8:
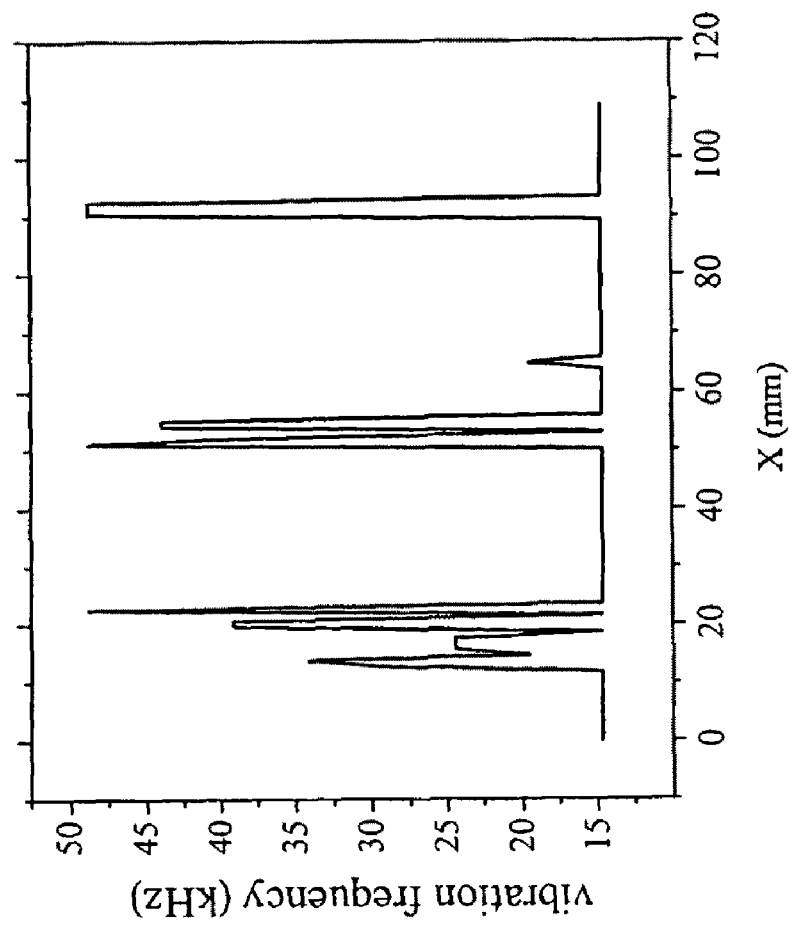
FIG. 8 is a graph of distribution of vibration frequencies (kHz) along the dotted line in FIG. 7.

The plot of FIG. 7 appears noisier, but it should be noted that some noise could originate from the honeycomb structure, the skin being itself a detached membrane within each honeycomb cell. It is also expected that when the laser beams are above a sufficiently large detachment but close to its edges, higher frequency vibration modes be excited. This has been noted previously and it is very useful for detecting large disbonds in a continuous scanning mode. This phenomenon is observed in FIG. 8.

Figure 9:
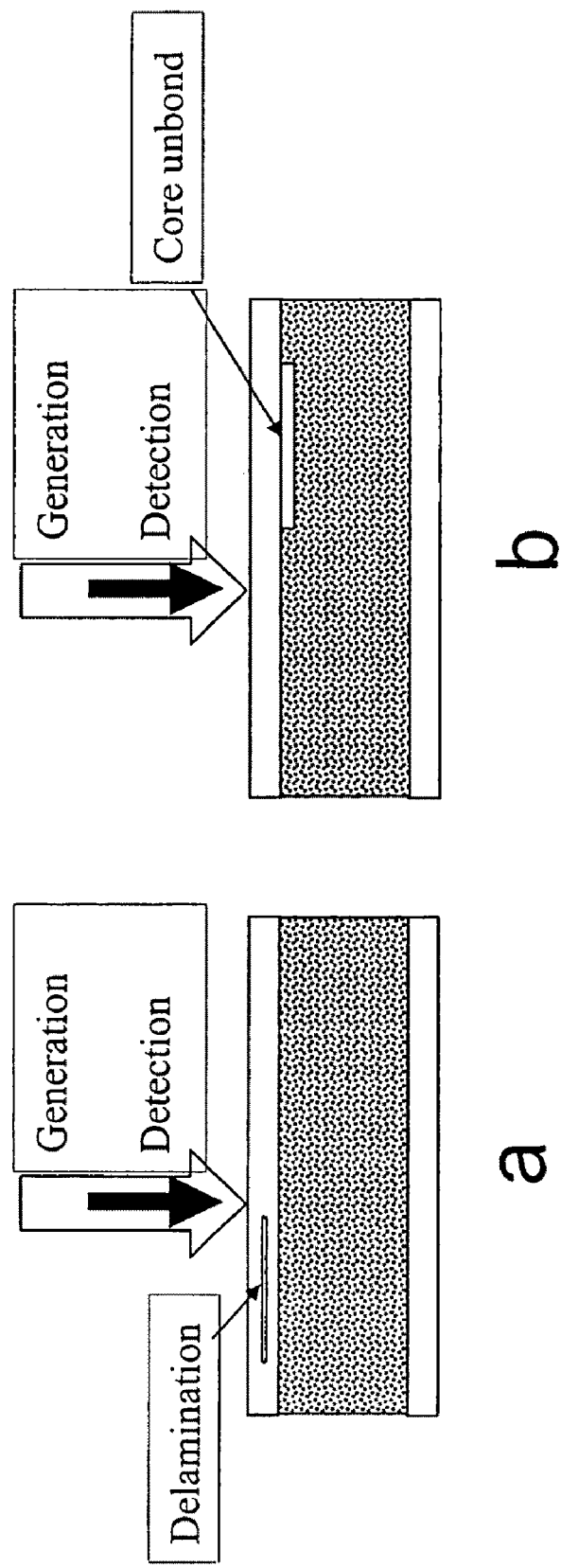
FIGS. 9 *a,b* is a schematic side view of a section of a foam core panel showing two kinds of disbonds: a delamination within a skin and a detached core.

The technique is obviously also applicable to foam core structures since these structures are made like honeycombs by bonding skins, which are usually laminates, to a core to rigidify the structure. Therefore delaminations in the skins and skin-core disbonds as sketched in FIGS. 9a-b can be detected with the proposed technique.

Figure 10:
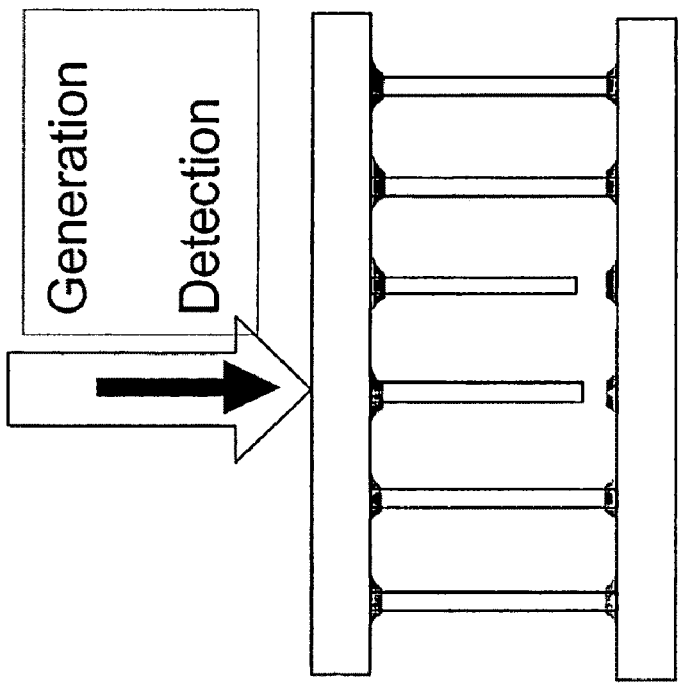
FIG. 10 is a schematic side view of a thin section of a honeycomb structure having core detached at the back of the honeycomb.
Figure 11:
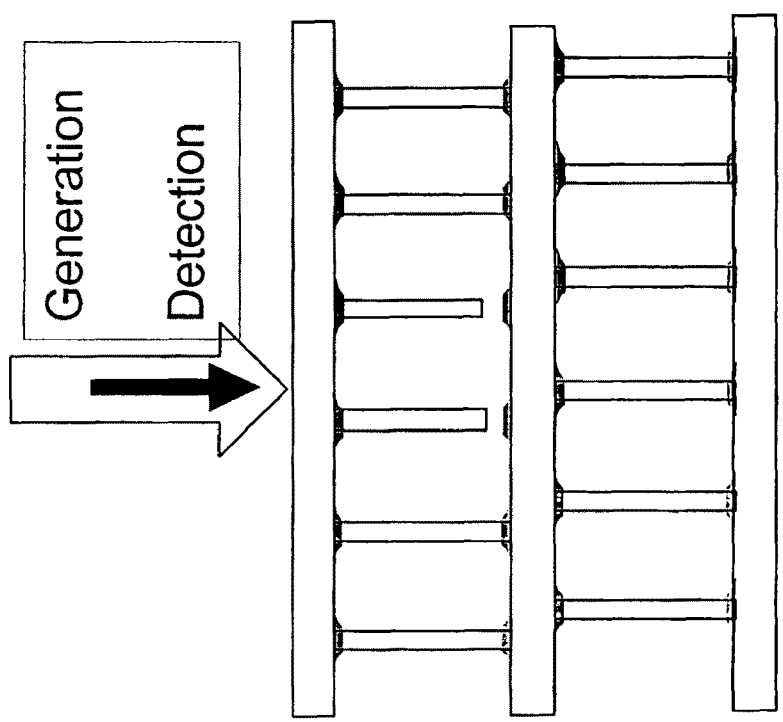
FIG. 11 is a schematic side view of a thin section of a paired honeycomb structure with a disbond occurring between a core layer and a distal skin.

The technique is also applicable to the embodiments of FIGS. 10 and 11, in which the disbond is located at the bottom of the honeycomb, between the honeycomb and a back or inner skin. In these embodiments, inspection is performed over a skin which is well bonded to the honeycomb. The embodiment of FIG. 10 is appropriate for an aircraft structure where the bottom or inner skin is not accessible. In the embodiment of FIG. 11, the inner skin is not obviously accessible. This embodiment presents an inspection challenge for the usual ultrasonic through-transmission technique: the transmitted signal tends to be very weak, since the two honeycombs are not usually matching, as sketched in FIG. 11. In these two cases the detached skin is not vibrating as a free membrane, but as a membrane stiffened by the bonded honeycomb. The vibration amplitude is then smaller and the vibration frequencies are higher. This can be qualitatively understood as if the Young's modulus of equation 1 was much higher.

In these cases, the vibration frequency being much higher, the stiffened membrane vibration may be found in the range of the frequency of the individual honeycomb cells or of the reverberating echoes within the top skin (if a sufficiently short pulse is used). Therefore, analysis to reveal inner disbond may be more difficult and spectral analysis has to be used. C-scan images plotting spectral components in various frequency bands are then displayed. Any amplitude change in one of these bands over one area compared to adjacent areas that cannot be explained by top skin detachment is indicative of detachment of the inner skin. Detachment of the top can be distinguished from detachment of the inner skin by the individual honeycomb cells resonances, which are more pronounced and as strong as in the adjacent areas in the case of detachment at the bottom. The signal being complex, time-frequency analysis may also be very helpful for identifying areas of disbond of the inner skin.

The technique is also applicable to cases similar to the ones depicted in FIGS. 10 and 11 with a foam core instead of a honeycomb core.

EXAMPLE 2

Anti-Wear Tungsten Carbide-Cobalt Coating on Steel

Figure 12:
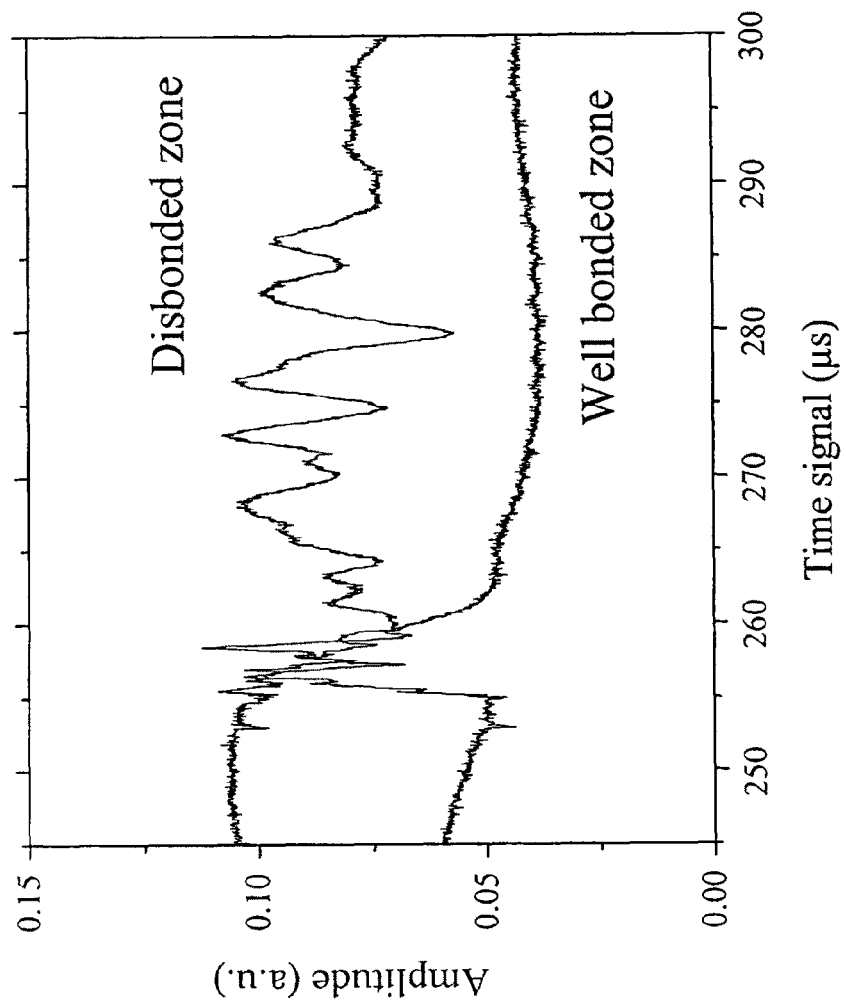
FIG. 12 is a graph superimposing plots of vibration amplitude as a function of time comparing well-bonded with disbanded positions of a hardness coating.
Figure 13:
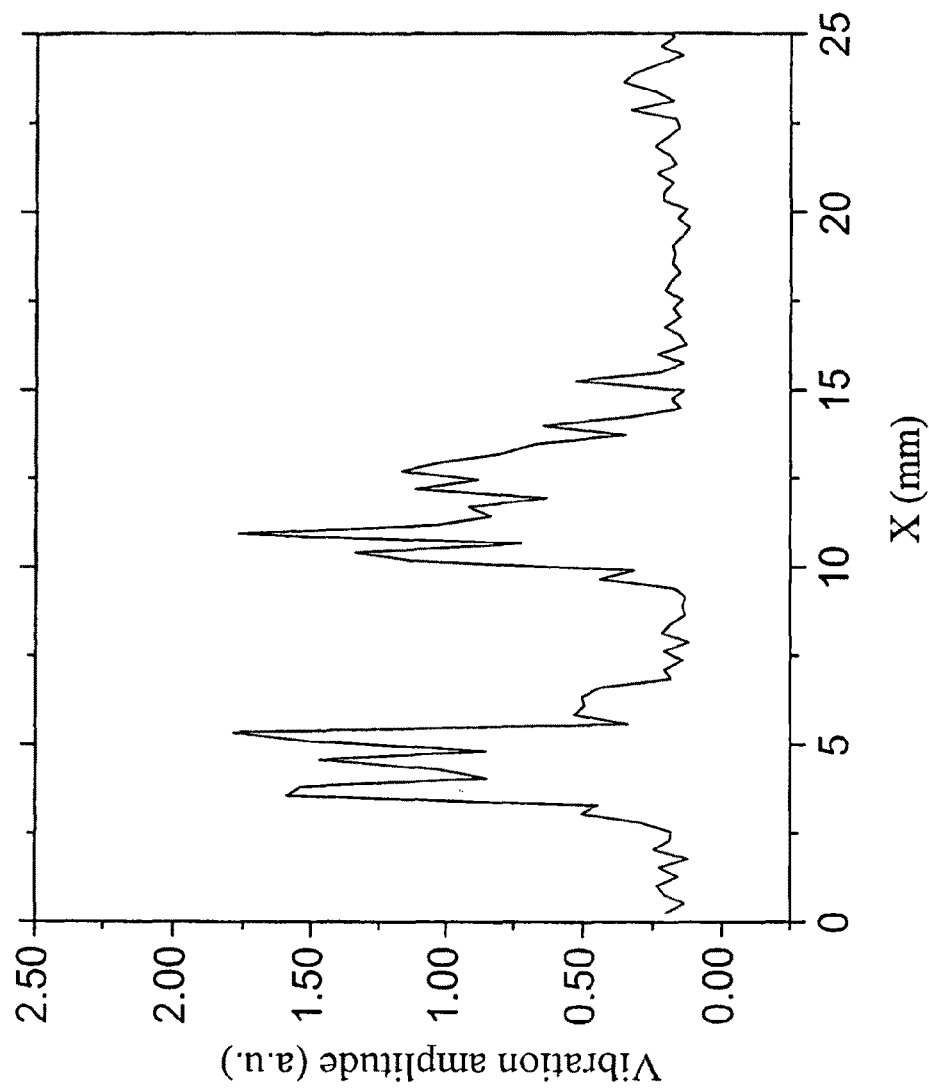
FIG. 13 is line scan showing a plot of vibration amplitude in a path demonstrating application of the invention to detecting disbond of a hardness coating.

With reference to FIGS. 12 and 13, example 2 demonstrates the detection of detachment of a Tungsten Carbide-Cobalt (WC—Co) coating on steel, although the technique is applicable to the detection of disbonds between an exposed first layer overlying a second material in general. These coatings are currently developed for replacing hard chromium coatings, which are at the source of known environmental problems. They are used on parts such as aircraft landing gears. These parts are subjected to fatigue cracking. Fatigue cracks may lead to detachment between the coating and the substrate, which are likely to follow by complete coating peel-off leaving the substrate unprotected from corrosion. Therefore the detection of such disbonds is very important.

In this case, the generation spot and the detection spot were slightly offset by about a spot size. In FIG. 12 one observes the arrival of a surface wave followed by a featureless trace when the interrogation is over a well bonded zone. When the interrogation is over a detached area, a strongly fluctuating signal is observed indicating the vibration of the detached membrane.

EXAMPLE 3

Silicon Carbide Protecting Layer on a Carbon-Carbon Substrate

Example 3 shows the detection of detachments occurring between a SiC oxidation protecting layer and a C—C substrate. Carbon-carbon substrates are widely used as thermal shields in rocket engines and on fuselages of space vehicles, such as the U.S. space shuttle. Since carbon is prone to reaction with oxygen above 450° C., C—C materials are generally protected by a ceramic coating such as one made of silicon carbide. The coating being porous, with time voids are produced by oxidation. If these voids grow bigger, the coating could get detached leaving the C—C substrate unprotected and subjected to severe oxidation. Therefore, the detection of disbonds between the coating and the C—C substrate is important.

Figure 14:
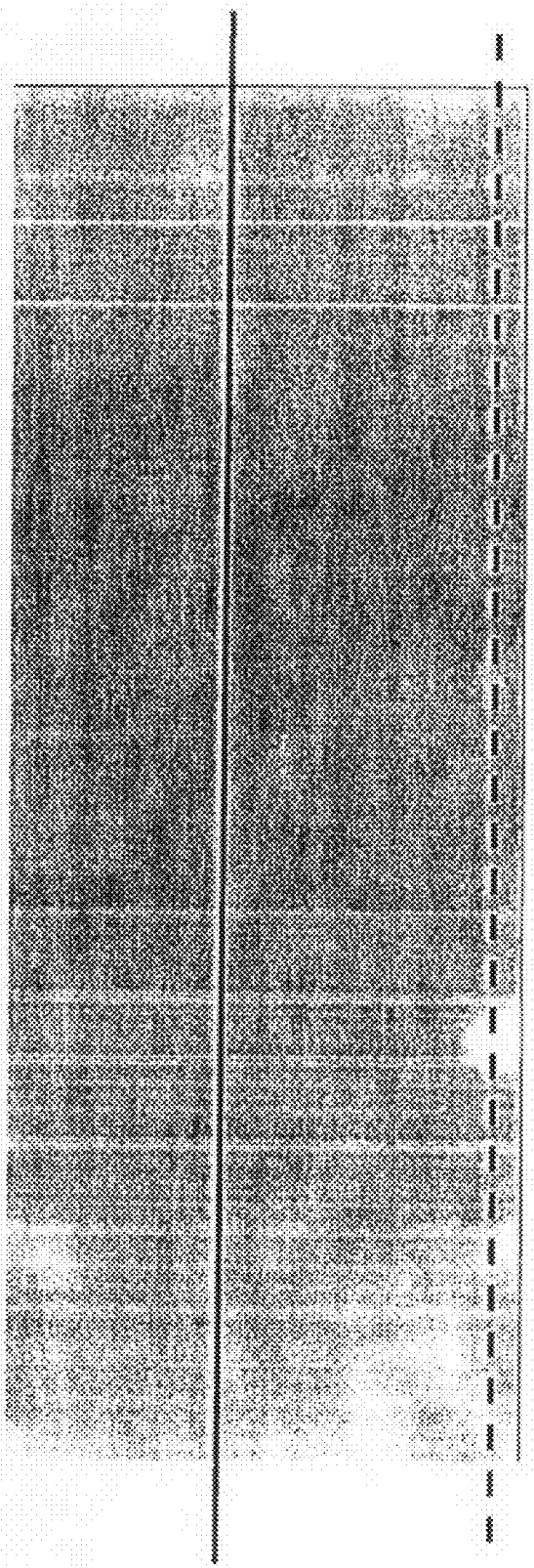
FIG. 14 is a C-scan image of maximum amplitude of the Fourier transform of the surface displacement of a carbon-carbon thermal barrier coating.
Figure 15:
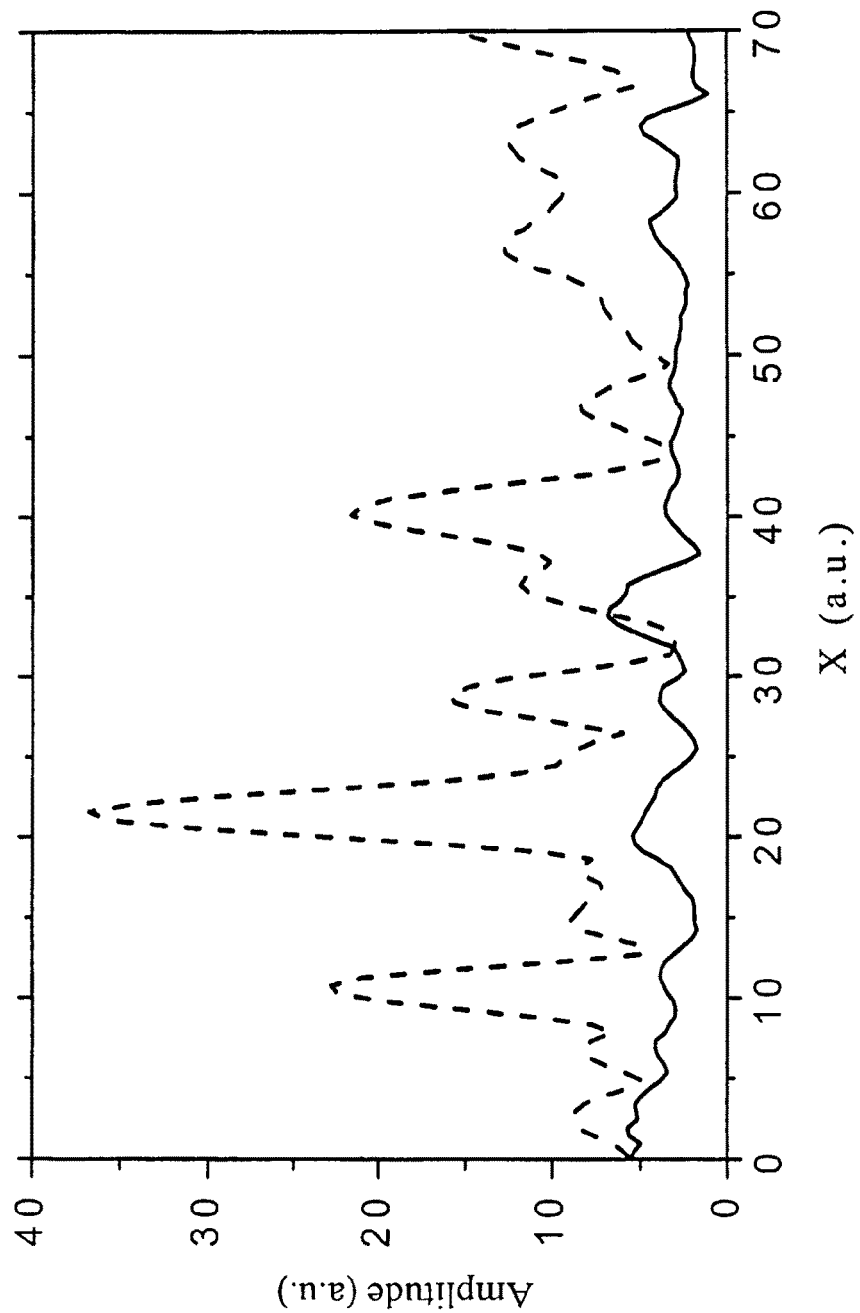
FIG. 15 is a graph superimposing plots of amplitude as a function of position comparing solid and dotted lines on the C-scan depicted in FIG. 14.

These coatings are however porous and strongly attenuate ultrasound, so pulse-echo ultrasonics does not work. Actually this approach was tried on the C—C sample used and no echo was observed. However, with the thermo-acoustic technique reported here, vibration signals are clearly observed when the coating is disbonded from the substrate. The experimental setup is similar to the one shown in FIG. 3a with overlapping generation and detection beams. The results obtained on this C—C sample with SiC coating protection are shown in FIGS. 14 and 15. FIG. 14 presents a C-scan of the amplitude of the Fourier transform of the data. Detachments are identified in the bottom of FIG. 14 near the edge of the specimen. Microscopic observation of the edges actually confirms that the coating is disbonded in these areas. These detachments are more clearly observed in FIG. 15, which plots the amplitude distribution along the dotted line shown in FIG. 14. For comparison, in FIG. 15, the amplitude along a well bonded line (solid line in FIG. 14) is also shown.

REFERENCES

[Cielo] Cielo et al. Pulsed dilatometric method and device for the detection of delamination, U.S. Pat. No. 4,752,140.

[Cielo2] P. Cielo, X. Maldague, G. Rousset, C. K. Jen. *Thermoelastic Inspection of Layered Materials: Dynamic Analysis, Materials Evaluation*, vol. 43, pp. 1111-1116, 1985

[Monch1] J.-P. Monclhalin, IEEE Trans on UFFC 33, 185- (1986).

[Monch2] J.-P. Monchalin, C. Néron, J. F. Bussière, P. Bouchard, C. Padioleau, R. Héon, M. Choquet, J.-D. Aussel, C. Carnois, P. Roy, G. Durou, J. A. Nilson, *Laser-ultrasonics: from the laboratory to the shop floor*, Advanced Performance Materials, vol. 5, pp. 7-23, 1998.

[Monch3] J.-P. Monchalin, M. Choquet, C. Padioleau, C. Néron, D. Lévesque, A. Blouin, C. Corbeil, R. Talbot, A. Bendada, M. Lamontagne, R. V. Kolarik II, G. V. Jeskey, E. D. Dominik, L. J. Duly K. J. Samblanet, S. E. Agger, K. J. Roush, M. L. Mester, *Laser-ultrasonic system for on-line steel tube gazuging*, Review of Progress in QNDE, AIP Conference Proceedings, vol. 22A, pp. 264-272, 2003.

[Blouin] A. Blouin and J.-P. Monchalin, *Detection of ultrasonic motion of a scattering surface by two-wave-mixing in a photorefractive GaAs crystal*, Appl. Phys. Lett., vol. 65, pp. 932-934, 1994.

[Kot] O. G. Kotiaevy, S. Uchida, *Nondestructive inspection of concrete structures with the use of photorefractive two-wave mixing*, SPIE Proceedings 4702, pp. 241-249.

[Petrov] M. P. Petrov, I. A. Sokolov, S. I. Stepanov, G. S. Trofimov, *Non-steady-state photo-electromotive-force induced by dynamic gratings in partially compensated photoconductors*, J. Appl. Phys. 68, 2216, (1990)

[Kamshilin] K. Päiväsaari, A. A. Kamshilin, *Adaptive sensors of rough-surface ultrasonic vibrations based on the polarization self-modulation effect*, Fourth International Conference on Vibration Measurements by Laser Techniques: Advances and Applications, SPIE Proceedings vol. 4072, 70, (2000).

[Pouet] B. Pouet, S. Breugnot, P. Clémenceau, *Innovative interferometer for industrial laser ultrasonic inspection*, Review of Progress in Quantitative Nondestructive Evaluation, AIP Conference Proceedings vol. 24, p. 273, (2005).

[Campagne] B. Campagne, A. Blouin, C. Néron, J.-P. Monchalin, *Doppler Frequency-Shift Compensated Photorefractive Interferometer For Ultrasound Detection On Objects In Motion*, Review of Progress in Quantitative Nondestructive Evaluation, AIP Conference Proceedings vol. 22, p. 273, (2003).

What is claimed is:

1. A method for assessing bond integrity at a region of a surface of a bonded material, the method comprising:
   a. producing transient heating in the region so that if the region overlies a disbond in the bonded material, membrane vibration having a vibration period is induced over the disbond; and
   b. detecting any surface displacement at or adjacent the region with a large etendue interferometer having a response time sufficiently short to adapt to ambient vibrations and speckle changes, but substantially longer than the vibration period;
   whereby the surface displacement can be used to determine whether a disbond is present.

2. The method of claim 1 wherein producing transient heating comprises applying a generation laser pulse having an intensity and wavelength to the surface sufficient to cause lifting of the disbonded material and to induce membrane vibration.

3. The method of claim 2 wherein the large etendue interferometer is based on one of: the photorefractive effect; the photoelectromotive force; and the polarization self-modulation effect.

4. The method of claim 2 wherein the large etendue interferometer is based on an array of interferometers followed by electronic processing, so as to use effectively a plurality of speckles.

5. The method of claim 2 wherein detecting any surface displacement comprises directing an interrogation laser beam of coherent light and a pump beam, both from a detection laser, onto a photorefractive material to produce a transient hologram within the photorefractive material.

6. The method of claim 5 wherein detecting any surface displacement comprises optically detecting interference of a reference beam produced by diffraction of the pump beam through the transient hologram, with respect to the interrogation beam.

7. The method of claim 5 wherein detecting any surface displacement comprises electrically detecting the transient hologram within the photorefractive material.

8. The method of claim 5 wherein directing the detection laser beam and directing the generation laser pulse onto the surface is performed by controlling a common set of optical components, such as by operating an intermittent or continuous beam moving device operable to scan across the surface of the bonded structure.

9. The method of claim 8 wherein controlling the common set of optical components involves operating a continuous beam moving device, and where detecting any surface displacement comprises applying a Doppler shift compensation using a velocity sensing arrangement and an acousto-optic shifter for frequency adjustment of one or both of the interrogation and pump beams.

10. The method of claim 2 wherein producing transient heating comprises applying a generation laser pulse having a pulse duration that is shorter than a time taken by an acoustic wave to pass through the membrane, reflect off a bottom thereof, and return to the surface, and the method further comprises analyzing a high frequency component of the detected surface displacement to obtain from a pulse echo interval, a thickness of the membrane.

11. The method of claim 10 wherein applying a generation laser pulse comprises applying the generation laser pulse for a duration less than 1 microsecond.

12. The method of claim 2 wherein detecting any surface displacement further comprises receiving a signal representing the surface displacement, and analyzing the signal to identify one of: a highest amplitude pulse in the time domain and a highest amplitude frequency in the frequency domain.

13. The method of claim 12 wherein the bonded structure has an exposed first layer overlying a second material, and the method further comprises:
   replicating the signal representing the surface displacement;
   high pass filtering the replica; and
   identifying one of a highest amplitude pulse within a time domain and a highest amplitude frequency within the frequency domain.

14. The method of claim 13 wherein the bonded structure is a honeycomb structured material having a honeycomb core sandwiched between two skins, the method further comprising:
   applying a spectral analysis of the signal to identify spectral components in one of a plurality of frequency bands for the region, and
   comparing the components within the region with those of other regions on the surface to identify a stiffened membrane vibration caused by a disbond between the honeycomb core and a distal one of the two skins.

15. The method of claim 13 wherein the bonded structure has a skin bonded to a core having a substantial proportion of material voids, and the method further comprises comparing a peak amplitude of the high pass filtered signal with that of the representative signal to determine whether the disbond is within the skin or between the skin and core.

16. The method as in claim 2 wherein producing transient heating in the region comprises applying sufficient energy to detach a stick bond.

17. An apparatus for assessing bond integrity at a region of a surface of a bonded material, the apparatus comprising:
   a. a generation laser beam for producing transient heating in the region so that if the region overlies a disbond in the bonded material, membrane vibration having a vibration period will be induced over the disbond;
   b. a large etendue interferometer for producing an interference in dependence on any surface displacement at the region, the large entendue interferometer having a response time sufficiently short to adapt to ambient vibrations and speckle changes, but substantially longer than the vibration period; and
   c. a detector for detecting the interference.

18. The apparatus of claim 17 wherein the large etendue interferometer operates on one of a photoelectromotive force effect; and a polarization self-modulation effect.

19. The apparatus of claim 17 wherein the large etendue interferometer consists of an array of single speckle interferometers the ouputs of which are compounded by electronic processing so as to effectively use a plurality of speckles.

20. The apparatus of claim 17 wherein large etendue interferometer comprises a beam splitter for separating a detection laser beam of coherent light into a pump beam, and an interrogation beam scattered off of the surface, and optical components for focusing the interrogation beam and pump beam onto a photorefractive material to produce a transient hologram within the photorefractive material.

21. The apparatus of claim 20 wherein the detector comprises an optical detector for detecting interference of a reference beam produced by diffraction of the pump beam through the transient hologram, with respect to the interrogation beam.

22. The apparatus of claim 20 wherein the detector comprises electrodes coupled to the photorefractive material for detecting a signal representative of the surface vibration.

23. The apparatus of claim 20 further comprising a beam moving device operable to scan the generation beam and interrogation beam across the surface of the bonded structure.

24. The apparatus of claim 23 further comprising a mechanism for moving the beam moving device to continuously scan the generation and interrogation beams across the surface, and the interferometer further comprises a Doppler frequency shift detection arrangement, as well as an acousto-optic shifter driven by the Doppler frequency shift detection arrangement for applying a frequency adjustment to one or both of the interrogation and pump beams to compensate for a Doppler shift.

25. The apparatus of claim 17 further comprising an analysis program for receiving a signal representing the detected surface displacement, and computing a highest amplitude frequency component.

26. The apparatus of claim 25 wherein the analysis program analyzing a high frequency component of the detected surface displacement to obtain from a pulse echo interval, the depth of the disbond.

27. The apparatus of claim 25 wherein the analysis program replicates a signal representing the surface displacement, high pass filters the replica, and identifies a highest amplitude pulse.

28. The apparatus of claim 25 wherein the bonded structure is a honeycomb structured material having a honeycomb core sandwiched between two skins, and the analysis program comprising spectral analysis program instructions for identifying spectral components in one of a plurality of frequency bands for the region, and comparing the components within the region with those of other regions on the surface to identify a stiffened membrane vibration caused by a disbond between the honeycomb core and a distal one of the two skins.

29. The apparatus of claim 27 wherein the bonded structure has a skin bonded to a substantially porous core, and the analysis program is further adapted to compare an amplitude and frequency of the high pass filtered signal with the representative signal to determine whether the disbond is within the skin or between the skin and core.

* * * * *